United States Patent
Gemmeke et al.

(10) Patent No.: US 8,884,793 B2
(45) Date of Patent: Nov. 11, 2014

(54) METHOD FOR REDUCING ULTRASOUND DATA

(75) Inventors: Hartmut Gemmeke, Stutensee (DE); Helmut Stripf, Eggenstein-Leopoldshafen (DE); Nicole Ruiter, Durmersheim (DE)

(73) Assignee: Karlsruher Institut Fuer Technologie, Karlsruhe (DE)

( * ) Notice: Subject to any disclaimer, the term of this patent is extended or adjusted under 35 U.S.C. 154(b) by 0 days.

(21) Appl. No.: 13/985,589

(22) PCT Filed: Feb. 14, 2012

(86) PCT No.: PCT/EP2012/000640
§ 371 (c)(1),
(2), (4) Date: Aug. 15, 2013

(87) PCT Pub. No.: WO2012/110228
PCT Pub. Date: Aug. 23, 2012

(65) Prior Publication Data
US 2013/0314260 A1  Nov. 28, 2013

(30) Foreign Application Priority Data
Feb. 17, 2011 (DE) .......... 10 2011 011 530

(51) Int. Cl.
*H03M 7/30* (2006.01)
*G01N 29/44* (2006.01)
*G01N 29/06* (2006.01)

(52) U.S. Cl.
CPC . *H03M 7/60* (2013.01); *H03M 7/30* (2013.01); *H03M 7/6058* (2013.01); *G01N 29/0672* (2013.01); *G01N 29/44* (2013.01); *G01N 29/4454* (2013.01); *G01N 2291/011* (2013.01); *G01N 2291/023* (2013.01); *G01N 2291/2636* (2013.01)
USPC ............. 341/76; 341/87; 702/189; 702/39; 702/171

(58) Field of Classification Search
None
See application file for complete search history.

(56) References Cited

U.S. PATENT DOCUMENTS

| | | | |
|---|---|---|---|
| 5,497,661 A | 3/1996 | Stripf et al. | |
| 5,635,645 A * | 6/1997 | Ottes et al. | 73/623 |
| 5,793,704 A | 8/1998 | Freger | |
| 6,826,982 B2 * | 12/2004 | O'Brien et al. | 73/587 |
| 7,657,403 B2 | 2/2010 | Stripf et al. | |
| 8,063,809 B2 * | 11/2011 | Liu et al. | 341/155 |

FOREIGN PATENT DOCUMENTS

| | | |
|---|---|---|
| DE | 4040190 A1 | 6/1992 |
| DE | 102005005386 B3 | 10/2007 |
| WO | WO 9826309 A1 | 6/1988 |

OTHER PUBLICATIONS

Serbian O. A., Grohs B., Licht R.: Signalanhebung durch Entstörung von Laufzeit-Messwerten aus Ultraschallprüfungen von ferritischen und austenitischen Werkstoffen—ALOK, Teil 1; Materialprüfung 23 (1981) pp. 379-383.

(Continued)

Primary Examiner — Howard Williams
(74) Attorney, Agent, or Firm — Leydig, Voit & Mayer, Ltd.

(57) ABSTRACT

A method for reducing ultrasound data from an ultrasound signal includes rectifying the ultrasound signal and generating an envelope curve about maximum values of the rectified ultrasound signal. Each ultrasound pulse is represented as a curve portion with a single maximum value. A first negative envelope curve signal, which is reduced by a first factor f, and a delayed envelope curve signal, which is not modified but is delayed by a time period $t_d$, are produced. The first negative envelope curve signal and the delayed envelope curve signal are added to form a first sum signal with a first zero crossing, wherein the first zero crossing represents a first time value. An amplitude is associated with the first time value, the amplitude corresponding to a signal height consistent with a maximum peak height from the envelope curve within a time interval about the first time value.

6 Claims, 4 Drawing Sheets

(56) References Cited

OTHER PUBLICATIONS

Balzer M et al. ,, Online data reduction with a dap-fpga multiprocessor system, Digital Processing, 2002. DSP 2002. 2002 14$^{th}$ International Conference on Santorini, Greece Jul. 1-3, 2002; Piscataway, NJ: USA,IEEE, US; vol. 2, Jul. 1, 2002, pp. 819-822.

Figueroa J F et al. 11A Method for Accurate Detection of Time of Arrival: Analysis and Design of an Ultrasonic Ranging System, The Journal of the Acoustical Society of America, American Institute of Physics for the Acoustical Society of America, New York, NY, US, Bd. 91, Nr. 1, Jan. 1, 1992 Seiten 486-494, XP888248408.

* cited by examiner

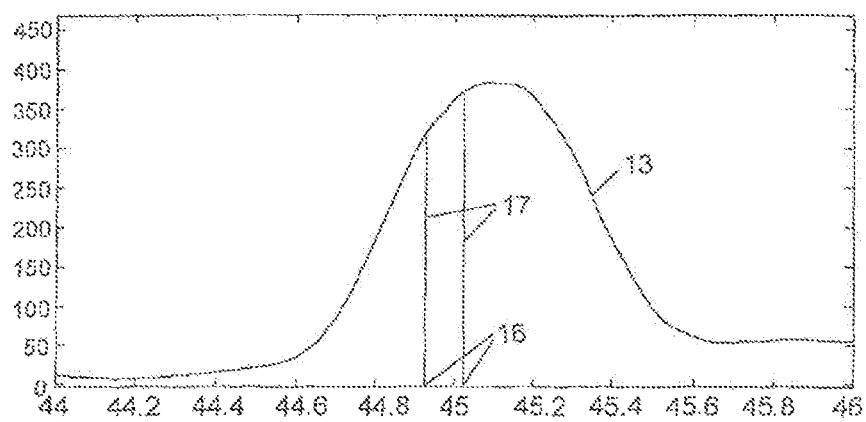
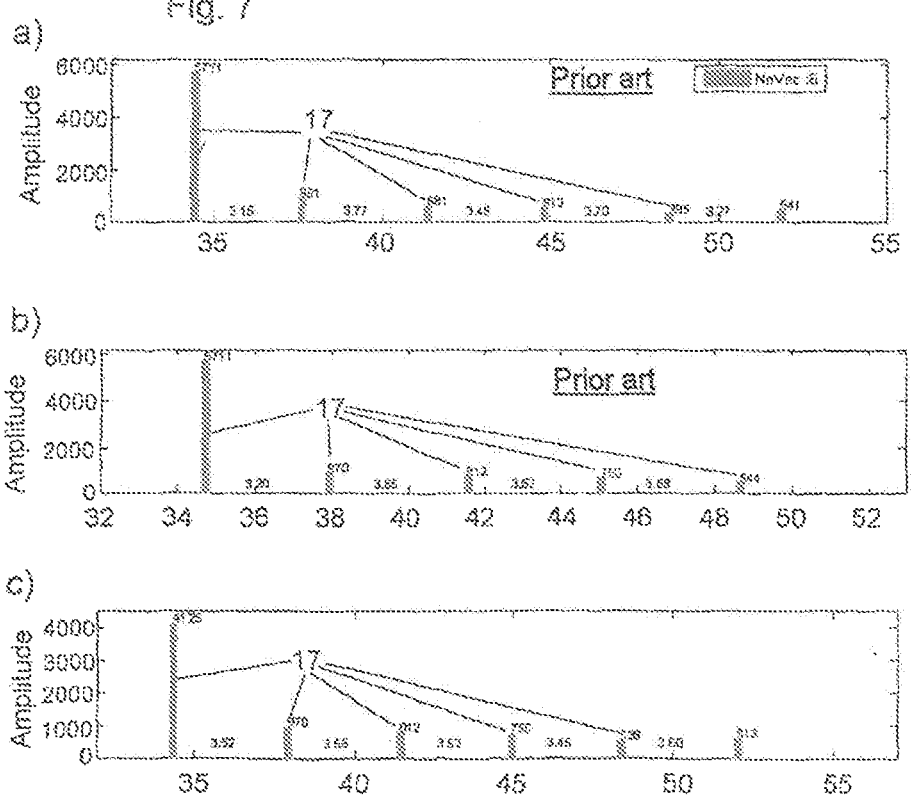

METHOD FOR REDUCING ULTRASOUND DATA

CROSS-REFERENCE TO PRIOR APPLICATIONS

This application is a U.S. National Phase Application under 35 U.S.C. §371 of International Application No. PCT/EP2012/000640, filed on Feb. 14, 2012, and claims benefit to German Patent Application No. DE 10 2011 011 530.7, filed on Feb. 17, 2011. The International Application was published in German on Aug. 23, 2012 as WO 2012/110228 under PCT Article 21(2).

FIELD

The invention relates to a method for reducing ultrasound data from an ultrasound signal comprising a plurality of ultrasound pulses.

BACKGROUND

An ultrasound signal is produced by exciting an ultrasonic transducer employed as a transmitter. Ultrasound is attenuated in the medium to be tested and/or is reflected at boundary surfaces. The ultrasound signal manipulated in this manner is subsequently received by an ultrasonic transducer employed as a receiver, the attenuation or reflection caused by the medium to be tested being detected, in addition to the transit time, by comparing the ultrasound signal transmitted and that received.

The measurement data obtained by the sensors are converted into electrical analogue signals and digitised in an analogue-to-digital converter to form digital ultrasound data. Said data contain the response signals which are produced in a through-transmission method or an echo method in response to an ultrasound signal and received by ultrasonic transducers. Examples of applications in which digitised ultrasound data are generated include medical ultrasound diagnosis and ultrasound-based material and component testing. In many of these ultrasound applications the data volume remains limited and it can therefore be stored without difficulty for subsequent offline evaluation. After being generated, the ultrasound data are passed on, either in real time or following intermediate storage, for subsequent, separate processing or use.

However, a significantly higher volume of ultrasound data is generated in complex ultrasound testing applications, for example tomography methods such as 3D ultrasound tomography methods (USCT) or ultrasound testing systems which operate independently over a longer period of time, for example crack or corrosion testing in pipes or pipelines. Processing said data in real-time, for example to produce tomography images, requires a very high degree of processing power. If it is not necessary to carry out a real-time evaluation, the data volumes must be stored in an intermediate manner in appropriately sized storage means.

"Testing pigs" which are provided with a large number of ultrasonic transducers (typically approximately 900 individual transducers) arranged circumferentially on the outer casing wall thereof are known, particularly in the field of pipeline testing, in particular oil or gas distribution pipelines. In order to examine the pipeline, the pig is inserted into the line and is transported through it along with the contents of the line. In this process, the condition of the pipeline is continuously examined by the transducers and the ultrasound data are stored inside the pig for subsequent evaluation. During the pig run through a long oil/gas line, very high data volumes accumulate owing to the large number of ultrasonic transducers on the one hand and the longer duration of the measurement sweeps through the pipeline on the other. In a pipeline test using a testing pig with 900 ultrasonic transducers, which operate at least in part in multiplex mode, at a test speed of 1 m/s (speed of the testing pig in the line), a data volume of approximately 900 TB accumulates over a pipeline distance of 500 km, at a data rate of approximately 2.8 GB/s. During a pig run of this type, this type of pig is not connected to the outside world. The data accumulated must therefore be stored in a form which allows the wall condition to be reconstructed outside the pipeline after the pig run, thus enabling the abnormalities/damage/defects in the pipe wall to be located and quantified reliably. Storing the data volumes accumulated does not appear practical or cost-effective, even with current storage media.

In medical sonography, in particular with complex applications such as tomography or high-resolution applications, very high data volumes also accumulate in a very short space of time, for example in the order of magnitude of 20 GB for medium-resolution tomographic mammography of a single breast. Although this very high data volume can be stored without difficulty in a stationary storage means, evaluating it without preselection requires very high and therefore expensive processing power on account of the high volume of raw data. To ensure that an image (reconstruction) can be produced in real time, the digital data obtained from the analogue values must be reduced/compressed.

In damage detection, data reduction methods therefore serve to extract the relevant features of a signal provided in connection with an anomaly or defect in the pipe wall or tissue and to reproduce them as accurately as possible in a minimum number of bits so as thereby to reduce/minimise the data volume to be stored.

It is essential to carry out data reduction to ensure that the data volume falls within a storable order of magnitude, that the run distance of the pig is cost-effective and that the intermediate storage means required for the testing pig or for ultrasound computed tomography is sufficient. Given that intermediate data storage prior to subsequent evaluation is not possible or is only possible with considerable storage space, in particular for independently operating systems such as the aforementioned pig systems, data reduction or data selection prior to storage is advisable.

Data reduction methods serve to extract all the features relevant for further processing from the ultrasound data and to save them in a reduced number of bits. It is possible to achieve considerably higher reduction factors through knowledge of the structure of the data and the weighting thereof, for example for the subsequent (offline) assessment of defects, by developing a specific reduction method adapted to the requirements of the signal evaluation.

One approach to this is disclosed in Barbian O. A., Grohs B., Licht R.: Signalanhebung durch Entstoerung von Laufzeit-Messwerten aus Ultarschallpruefungen von ferritischen und austenitischen Werkstoffen—ALOK, Part 1; Materialpruefung 23 (1981) 379-383. The method described in said document selects the peaks of an ultrasound signal envelope on the basis of the maximum values of half-waves. In a signal sequence comprising a number of repeating half-wave amplitudes of similar height, as measured in particular in the ultrasound echo method, selecting peak values in the assessment of the transit time is, however, subject to substantially greater variation in comparison with assessing the time from the slope of the envelope.

DE 40 40 190 A1 discloses a reduction method in which the time and amplitude are detected for the maximum value, for every digitally filtered reflected pulse. This method does not, however, evaluate the width and characteristic curve of the envelopes, and this leads to inaccuracies, in particular when assessing the pulse height. Moreover, the method requires an ultrasound signal smoothed by a low-pass filter.

DE 10 2005 005 386 B3 further discloses a method for specifically reducing digitised data from a large number of electromagnetic measurement transducers in an "EMAT pig" (electromagnetic acoustic transducer) to detect defects in sheet metal or pipes. The method is based on an algorithm for selecting maximum values from a sequence of peak values of the measured values and comprises an assessment of the size of a defect and of the signal background in the region surrounding a defect. The transit times must, however, be assessed accurately to compress the data of an ultrasound echo signal sequence with a plurality of peak values of virtually the same amplitude, and said method is too inaccurate.

SUMMARY

In an embodiment, the present invention provides a method for reducing ultrasound data from an ultrasound signal comprising a plurality of ultrasound pulses. The ultrasound signal is rectified. An envelope curve is generated about maximum values of the rectified ultrasound signal, wherein each of the ultrasound pulses is represented as a curve portion with a single maximum value. A first negative envelope curve signal is produced, which is reduced by a first factor f, and a delayed envelope curve signal is produced, which is not modified but is delayed by a time period td, for each of the ultrasound pulses. The first negative envelope curve signal and the delayed envelope curve signal are added to form a first sum signal with a first zero crossing, wherein the first zero crossing represents a first time value. An amplitude is associated with the first time value, the amplitude corresponding to a signal height consistent with a maximum peak height from the envelope curve within a time interval about the first time value.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIG. 6 shows the envelope curve signal from FIGS. 3 and 5, with two ultrasound vectors at zero crossings with different fs, and FIGS. 7a-c show vectorisations, with FIGS. 7a and 7b being from the prior art.

DETAILED DESCRIPTION

In an embodiment, the invention provides a method for reducing digital ultrasound measurement data obtained from measurement values which makes it possible to reduce data by a factor of from 10 to 500 and provides, in comparison with the cited prior art, improved detection of transit times and pulse heights of ultrasound pulses in particular.

In an embodiment, the main method steps are based on a value selection algorithm which provides amplitude-transit time pairs (vectors) which indicate the maximum values of the ultrasound envelopes. In this document, the transit time pairs will be referred to as vectors.

The method for reducing ultrasound data from an ultrasound signal according to an embodiment preferably comprises the following method steps:

1. Rectifying the ultrasound signal:
   This step basically comprises the conversion of the negative polarity signal portions into positive signal portions, i.e. folding back the signals into the positive voltage range. The ultrasound data are optionally filtered beforehand.
2. Generating an envelope curve for the rectified ultrasound signal, oriented relative to the maximum values (envelope), the ultrasound pulses being represented as single maximum values,
3. Generating a negative envelope curve signal which is reduced by a factor of preferably between 0.2 and 0.8, more preferably between 0.3 and 0.6, and a non-modified but delayed envelope curve signal,
4. Adding the negatively reduced envelope curve signal and the delayed envelope curve signal to form a sum signal, the sum signal having a zero crossing and the zero crossing representing a time value (trigger signal), and
5. Associating an amplitude with the time value, the amplitude corresponding to a signal height consistent with a maximum peak height from the envelope curve within a time interval about the time value.

The method for reducing ultrasound data from an ultrasound signal makes it possible to reduce the data obtained in an ultrasound-based pipeline test by a preferred factor of from approximately 100 to 300 depending on the condition of the pipeline and, in ultrasound-based organ tissue examinations, by a preferred factor of from 10 to 20. The reduced data volume can then be saved on robust, shock- and temperature-resistant mass storage means.

Figure 1:
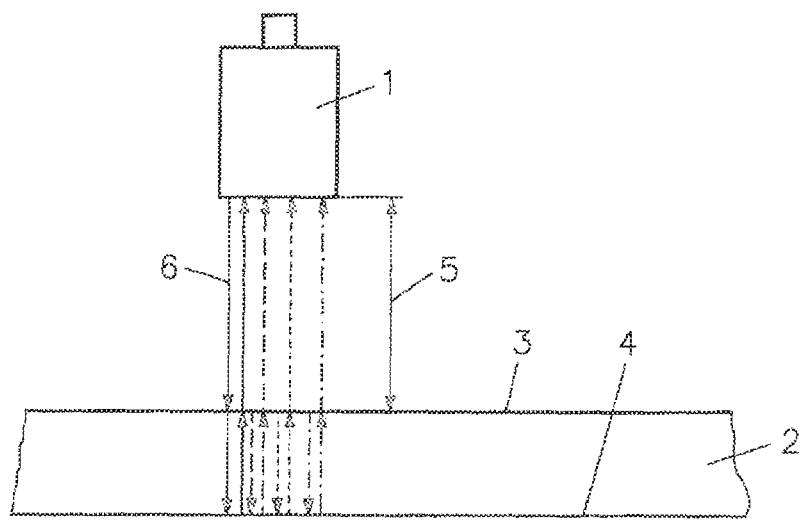
FIG. 1 shows, by way of example, a construction and the ultrasound signal pathways in ultrasound-based wall thickness measurement (pulse-echo method).

The basic arrangement of an ultrasound system on an object to be tested (pipe wall) is shown by way of example on a plate in FIG. 1 as a simplified diagram. A standoff distance 5 is provided between the ultrasound probe 1 of the ultrasound system and the object to be tested (a pipe wall 2 with internal and external walls 3 and 4 respectively as reflection planes). The standoff distance serves to set a particular time delay between the transmission signal and the first pulse signal that may be received from the closest reflection plane. It generally extends through a liquid or solid medium and is thus an integral part of an ultrasound system.

The arrangement corresponds in principle to that used for diagnostic sonography, but the reflection planes and the tissue to be examined in that case would lead to more diffuse echo pulses.

The ultrasound pulse triggered by an excitement pulse at the ultrasound probe 1 passes through a standoff distance 5 and is reflected in part by the internal wall 3, returning to the ultrasound probe. The remaining sound energy penetrates into the pipe wall 2 made for example from steel and is for the most part reflected by the external wall 4 of the pipe. Some of said energy returns to the ultrasound probe (first back wall echo signal), as viewed from the inside to the outside of the pipe, and the remainder is again reflected inwards by the internal wall. Some of said remaining signal, which is reflected into the wall by the internal wall of the pipe, is again transmitted outwards at the external wall 4 and the remainder is reflected inwards, to be in turn partly transmitted inwards at the internal wall 3 and received by the ultrasound probe as the second back wall echo signal. The portion reflected by the internal wall 3 into the wall interior in the direction of the external wall 4 is again transmitted and/or reflected again as described above when it reaches the external wall. The portion reflected at the outer wall which is subsequently transmitted again at the internal wall finally enters the ultrasound probe as a third back wall echo. Depending on the sound attenuation, there may be further reflection within the pipe wall. The individual sound pathways are shown schematically by arrows 6, each return path caused by reflection being offset to the right for visual clarity and the second and fourth back wall echoes being indicated as broken lines.

Based on the known sound speed in the wall material and the time measured between the individual echoes, it is possible to measure the sound transit times through the pipe wall and thus determine the thickness of the pipe wall.

The findings shown in the following figures have been obtained from an ultrasound wall thickness measurement procedure carried out on pipeline walls from the interior of the pipe using the pig systems mentioned at the outset. In this case, vectorisation may be used as a measure of the quality of the method. In the case of ideal vectorisation, the time gap between the individual vectors is constant.

The following data reduction method is broken down into the following basic steps/methods, only steps 1 and 3 (in the described form or a modified form thereof) being mandatory in an embodiment, whereas the other steps mentioned serve as other advantageous embodiments:

1. Rectification and Envelopment of the Ultrasound Signal

Figure 2A:
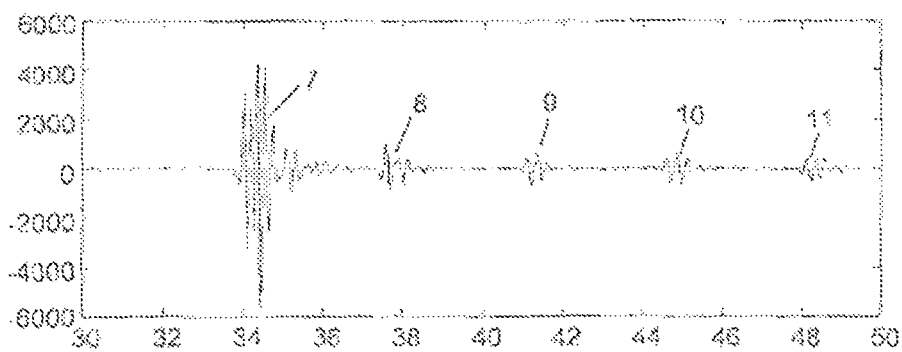
FIG. 2a shows an ultrasound signal received by an ultrasound probe in the configuration shown in FIG. 1.

FIG. 2a reproduces the signal curve of the echo pulses received by the ultrasound probe 1 over time. Adjacent to the first back wall echo 7, the second, third, fourth and fifth back wall echoes 8 to 11 of the ultrasound pulse are shown without further postprocessing. The region before the first back wall echo is determined by the transit time through the standoff distance. Each time gap between the individual back wall echoes is identical and corresponds to double the transit time through the pipe wall.

Figure 2B:
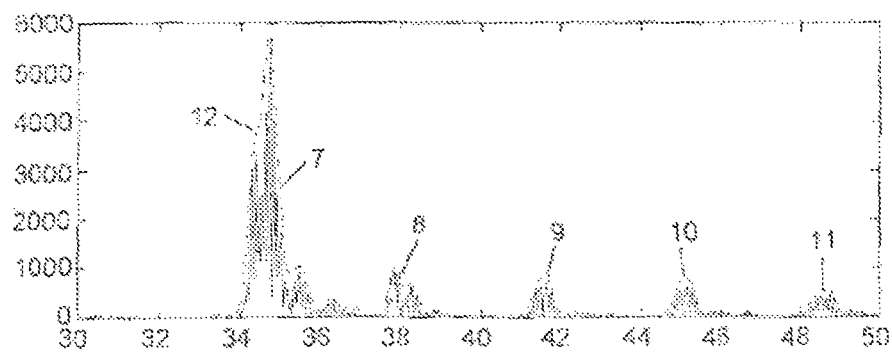
FIG. 2b shows the rectified ultrasound signals from FIG. 2a, with the envelope curve.
Figure 3:
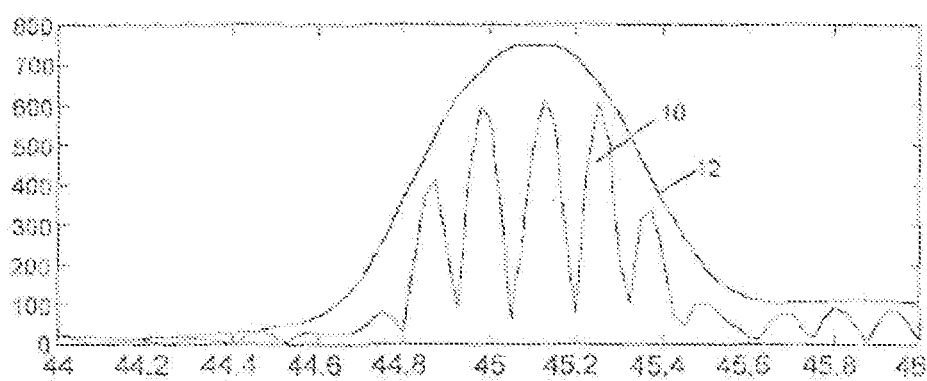
FIG. 3 shows a detail enlargement for the time interval about the third minor maximum (ultrasound pulse) from FIG. 2b.

In a first step, the signal received is rectified and provided with an envelope curve 12 (envelope) (FIG. 2b) which is oriented relative to the respective maximum values of the rectified signal. The rectified echo signal is reproduced in FIG. 3 for the period of time around the fourth back wall echo. Like the other back wall echoes, it comprises a plurality of oscillations which are frequently of virtually the same amplitude, as is typical of pulsed excitation of weakly damped ultrasound probes in particular.

The ultrasound echo envelope is preferably obtained by a digital low-pass filter, particularly preferably a CIC filter (cascaded integrator-comb filter). A CIC filter is a particular type of digital FIR filter which can very advantageously be implemented in digital hardware such as FPGAs (field-programmable gate arrays), since all the filter coefficients are "1" and therefore no computationally intensive multiplication is required (see FIG. 2b and FIG. 3).

2. Non-amplitude-dependent Triggering of Transit Time Assessment

Figure 4:
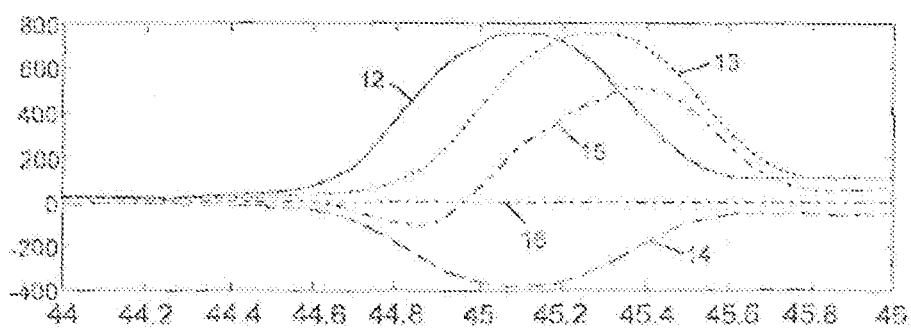
FIG. 4 shows the envelope curve signal from FIG. 3, a negative envelope curve signal which has been reduced by a factor of from 0.3 to 0.6 an envelope curve signal which has not been modified but has been delayed by a time period $t_d$ and a sum signal, formed from the negatively reduced and delayed envelope curve signals, with a zero crossing.

The transit time is calculated by an envelope signal edge trigger (discrimination) algorithm, independently of the signal height. In this case, the trigger is not activated by the signal exceeding or passing above a predetermined fixed threshold, but is rather activated when a particular signal height is achieved as a function of the maximum pulse height (generally between 0.3 and 0.6 of the pulse height of each back wall echo or the envelope thereof) For this purpose, the rectified and enveloped signal (envelope curve 12) is fed into two different paths. In one path, it is delayed to form a delay signal 13 (delayed envelope curve signal). In the other path, the same rectified and enveloped signal is weakened by a particular division factor f to form an attenuated signal, and is folded back to form an inverted attenuated envelope curve signal 14 (see FIG. 4). The inverse attenuated signal is added to the delay signal to form a sum signal 15, in accordance with $$A_{res}(t) = A_e(t-t_d) - f \cdot A_e(t), \tag{1}$$

$A_{res}$ being the amplitude of the resultant signal, $A_e$ being the amplitude of the input signal and $t_d$ being the time by which the input signal is delayed.

The positive zero crossing 16 of the signal $A_{res}$ (FIG. 4) is then defined as the trigger time $t_{trigger}$. This time $t_{trigger}$ is dependent on the gradient m of the pulses ($m = \Delta A/\Delta t$), the fraction f and the delay $t_d$ ($t_{trigger} = t_{trigger}(m, f, t_d)$), but not on the amplitude height.

3. Amplitude Assessment

Figure 5:
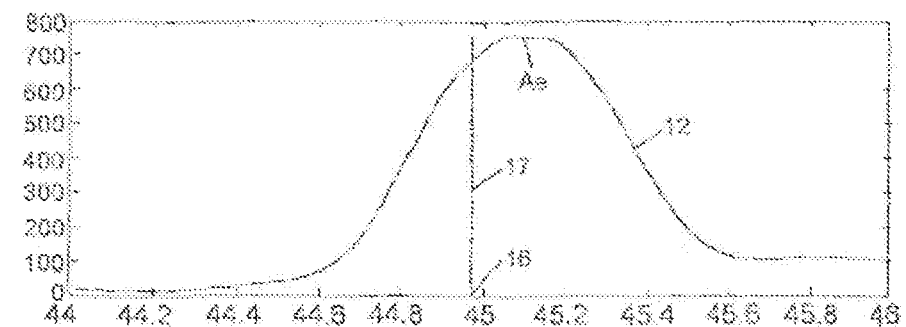
FIG. 5 shows the envelope curve signal from FIG. 3 and an ultrasound vector at the time of the zero crossing in FIG. 4, showing the maximum height of the ultrasound curve signal.

The delay time $t_d$ is selected in such a way that the trigger time $t_{trigger}$ lies in the amplitude range of the input signal $A_e$. The maximum value of $A_e$ is then assessed and saved in the storage means as the amplitude value $A_m$ in a defined time range about the time value $t_{trigger}$. The amplitude-transit time pair $A_m$ and $t_{trigger}$ thus describe the ultrasound vector 17 (see FIG. 5).

4. Vector Selection

Vectors with amplitudes which lie below an adjustable, parameterised threshold are optionally eliminated. This eliminates noise signals.

5. Options

The dependence of the trigger time on the gradient m of the signal may be used to assess or characterise the shape of the envelope. The difference in the trigger time in the case of different reduction factors f is a measure of the steepness m and therefore a measure of the shape of the signal (see FIG. 6). If this difference value is stored in addition to the amplitude and transit time, the assessment of defects carried out offline can be made more accurate.

The method explained with reference to FIG. 6 includes the production of a second negative envelope curve signal which has been reduced in the example by a second factor f=0.6 different to the first factor f=0.4, and an envelope curve signal which has not been modified but has been delayed by a time period $t_d$, for each ultrasound pulse. The second negatively reduced envelope curve signal and the delayed envelope curve signal are added to form a second sum signal with a second zero crossing, the second zero crossing representing a second time value, and a gradient is associated with the first and second time values as described above. In this case, the time value is determined from the time period from the first and second time values and the difference signal of the envelope curve signal between the signal values of the first and second time values.

FIGS. 7a to c show the comparative vectorisation of ultrasound data from an ultrasound output signal received by the ultrasound probe as obtained in various methods, using the example of an ultrasound signal from a wall thickness measurement (cf. FIG. 2a). Each time gap between the individual back wall echoes is identical and corresponds to double the transit time through the pipe wall. In the case of optimal vectorisation, the time gap between the individual vectors is also constant, for which reason the time gaps have been used to compare different methods.

The variance in the aforementioned time gaps between the vectors is used as a measure of vectorisation quality.

FIG. 7a shows the vectorisation achieved based on selecting maximum values from a sequence of peak values in accordance with the prior art DE 10 2005 005 386 B3; the variance between the time differences is 71.6 ns.

If, instead of half-wave maximum values being selected, a CIC is used to form envelopes and to subsequently detect the peak values in accordance with the prior art DE 40 40 190 A1 (see FIG. 7b), the variance between the time differences falls to 39.4 ns.

In contrast, FIG. 7c shows the vectorisation in accordance with a method comprising the aforementioned rectification and envelopment of the ultrasound signal, non-amplitude-dependent triggering of the transit time assessment and amplitude assessment (cf. FIGS. 2b to 5). The variance in the time gaps is reduced to 2.9 ns.

In comparison with the cited prior art, the method described yields a significant improvement in vectorisation, particularly in the time assessment. This can significantly improve the accuracy for example of the wall thickness measurement.

In addition, with regard to medical ultrasound diagnosis, such as ultrasound computed tomography (USCT), this more precise time measurement makes it possible to achieve a more accurate measurement of speed and thus also more precise spatial resolution in different tissue.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS

1 Ultrasound probe
2 Pipe wall
3 Internal wall
4 External wall
5 Standoff distance
6 Arrows
7 First back wall echo
8 Second back wall echo
9 Third back wall echo
10 Fourth back wall echo
11 Fifth back wall echo
12 Envelope curve
13 Delay signal
14 Inverse attenuated signal
15 Sum signal
16 Zero crossing
17 Vector

The invention claimed is:

1. A method for reducing ultrasound data from an ultrasound signal comprising a plurality of ultrasound pulses, the method comprising:
  a) rectifying the ultrasound signal,
  b) generating an envelope curve about the maximum values of the rectified ultrasound signal, wherein each of the ultrasound pulses is represented as a curve portion with a single maximum value,
  c) producing a first negative envelope curve signal, which is reduced by a first factor f, and a delayed envelope curve signal, which is not modified but is delayed by a time period $t_d$, for each of the ultrasound pulses,
  d) adding the first negative envelope curve signal and the delayed envelope curve signal to form a first sum signal with a first zero crossing, wherein the first zero crossing represents a first time value, and
  e) associating an amplitude with the first time value, the amplitude corresponding to a signal height consistent with a maximum peak height from the envelope curve within a time interval about the first time value.

2. The method according to claim 1, wherein the time interval is delimited by a full width at half maximum of the envelope curve about the first time value.

3. The method according to claim 1, further comprising:
  a) producing a second negative envelope curve signal, which is reduced by a second factor different to the first factor, and a delayed envelope curve signal, which is not modified but is delayed by a time period $t_d$, for each of the ultrasound pulses,
  b) adding the second negative envelope curve signal and the delayed envelope curve signal to form a second sum signal with a second zero crossing, wherein the second zero crossing represents a second time value, and
  c) associating a gradient with the first and second time values, wherein a third time value is determined from a time period from the first and second time values and a difference signal of the envelope curve signal between signal values of the first and second time values.

4. The method according to claim 3, wherein each time value, together with the associated amplitude, and each time value pair, together with the associated gradient, form a vector, and the vectors with amplitudes which fall below a threshold value are removed from the ultrasound data.

5. The method according to claim 1, further comprising:
  a) producing a second time value at a time of an increasing full width at half maximum of the envelope curve, prior to the first time value, and b) associating a gradient with the first and second time values, wherein a third time value is determined from a time period from the first and second time values and a difference signal of the envelope curve signal between signal values of the first and second time values.

6. The method according to claim 1, wherein the factor is constant and lies between 0.3 and 0.6.

* * * * *